(12) United States Patent
Nanri et al.

(10) Patent No.: US 10,233,548 B2
(45) Date of Patent: Mar. 19, 2019

(54) CHARGED PARTICLE BEAM DEVICE AND SAMPLE PRODUCTION METHOD

(75) Inventors: Terutaka Nanri, Hitachinaka (JP); Tsuyoshi Onishi, Hitachinaka (JP); Satoshi Tomimatsu, Hitachinaka (JP)

(73) Assignee: HITACHI HIGH-TECHNOLOGIES CORPORATION, Tokyo (JP)

( * ) Notice: Subject to any disclaimer, the term of this patent is extended or adjusted under 35 U.S.C. 154(b) by 844 days.

(21) Appl. No.: 13/808,261

(22) PCT Filed: Jul. 5, 2011

(86) PCT No.: PCT/JP2011/065324
§ 371 (c)(1),
(2), (4) Date: Jan. 4, 2013

(87) PCT Pub. No.: WO2012/005232
PCT Pub. Date: Jan. 12, 2012

(65) Prior Publication Data
US 2013/0105302 A1    May 2, 2013

(30) Foreign Application Priority Data
Jul. 7, 2010    (JP) .................................. 2010-154871

(51) Int. Cl.
*C23C 14/34*    (2006.01)
*C23F 4/02*    (2006.01)
(Continued)

(52) U.S. Cl.
CPC .................. *C23F 4/02* (2013.01); *G01N 1/32* (2013.01); *G01N 23/225* (2013.01); *H01J 37/08* (2013.01);
(Continued)

(58) Field of Classification Search
CPC ....... H01J 37/08; H01J 37/244; G01N 23/225
See application file for complete search history.

(56) References Cited

U.S. PATENT DOCUMENTS 5,574,280 A * 11/1996 Fujii .................... H01J 37/3056
250/492.21
5,952,658 A *  9/1999 Shimase ............... H01J 37/304
250/492.21
(Continued)

FOREIGN PATENT DOCUMENTS

JP    6-260129    9/1994
JP    7-134967    5/1995
(Continued)

OTHER PUBLICATIONS

Communication pursuant to Article 94(3) EPC, dated Apr. 5, 2018, which issued during the prosecution of European Patent Application No. 11 803 566.6, which corresponds to the present application.

*Primary Examiner* — Jason Berman
(74) *Attorney, Agent, or Firm* — Baker Botts L.L.P.

(57) ABSTRACT

Provided is a technique capable of removing a damaged layer of a sample piece generated through an FIB fabrication sufficiently but at the minimum. A charged particle beam device includes a first element ion beam optical system unit (110) which performs a first FIB fabrication to form a sample piece from a sample, a second element ion beam optical system unit (120) which performs a second FIB fabrication to remove a damaged layer formed on a surface of the sample piece, and a first element detector (140) which detects an first element existing in the damaged layer. A termination of the second FIB fabrication is determined if an amount of the first element existing in the damaged layer becomes smaller than a predefined threshold value.

17 Claims, 12 Drawing Sheets

(51) Int. Cl.
  *H01J 37/08* (2006.01)
  *G01N 23/225* (2018.01)
  *H01J 37/244* (2006.01)
  *G01N 1/32* (2006.01)
  *H01J 37/30* (2006.01)
  *H01J 37/305* (2006.01)

(52) U.S. Cl.
  CPC ........ *H01J 37/244* (2013.01); *H01J 37/3002* (2013.01); *H01J 37/3056* (2013.01); *H01J 2237/31745* (2013.01)

(56) References Cited

U.S. PATENT DOCUMENTS

| | | | |
|---|---|---|---|
| 6,281,025 | B1 | 8/2001 | Ring et al. |
| 2002/0017619 | A1* | 2/2002 | Hirose ................ H01J 37/3005 250/492.3 |
| 2004/0262515 | A1 | 12/2004 | Motoi et al. |
| 2006/0145090 | A1* | 7/2006 | Ohtsuka ................. B82Y 10/00 250/425 |
| 2006/0163497 | A1* | 7/2006 | Kodama ............. H01J 37/3056 250/492.21 |
| 2010/0059672 | A1 | 3/2010 | Zeile |
| 2010/0288924 | A1 | 11/2010 | Kaito et al. |

FOREIGN PATENT DOCUMENTS

| | | |
|---|---|---|
| JP | 10-223574 | 8/1998 |
| JP | 2001-345360 A | 12/2001 |
| JP | 2003-194746 | 7/2003 |
| JP | 2004-95339 | 3/2004 |
| JP | 2007-108105 | 4/2007 |
| JP | 2007-193977 | 8/2007 |
| WO | WO 2009/020151 | 2/2009 |

\* cited by examiner

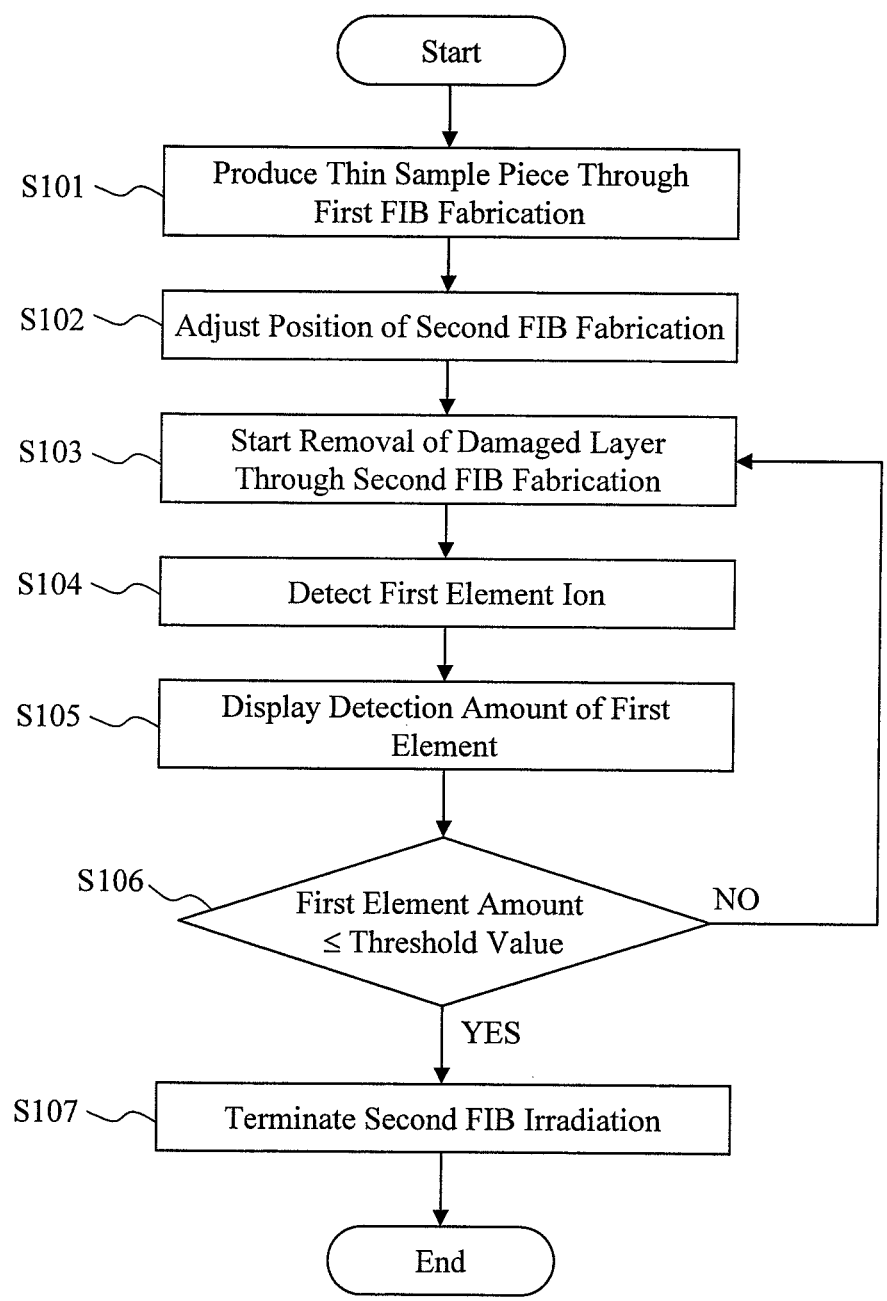

CHARGED PARTICLE BEAM DEVICE AND SAMPLE PRODUCTION METHOD

TECHNICAL FIELD

The present invention relates to a technique of a production method of a sample for an electron microscopic observation by means of a charged particle beam device.

BACKGROUND ART

As a circuit pattern refinement of a semiconductor device is enhanced, inspecting electrical defects and finding out causes of the defects become a more crucial issue. In particular, a defect analysis to cut and fabricate a sample, and analyze the shape and material of the sample is growing in importance for investigating the causes of the defects. An analysis using a transmission electron microscope (referred to as a "TEM", hereinafter) or a scanning transmission electron microscope (referred to as a "STEM", hereinafter) is essential in refinement of a circuit pattern at a nanometer level, and such an analysis requires a technique to precisely and accurately prepare a desirable sample for an electron microscopic observation.

An observation sample for a TEM or a STEM is prepared into a thin sample piece having a thickness of approximately 100 nanometers, which allows an electron beam to transmit the sample. A focused ion beam (referred to as "FIB", hereinafter) fabrication device is used for producing such a thin sample piece. The FIB fabrication device focuses an ion beam into a fine spot, so as to fabricate the sample through an electrostatic deflection scanning.

The prepared thin sample piece through the FIB fabrication has a damaged layer on its surface. The damaged layer is formed such by ions entering the inside of the sample, and converting a crystal structure into an amorphous structure thereof. The damaged layer is also produced in an interface between different materials. This damaged layer deteriorates transmitting performance of the electron beam relative to the sample when a TEM or a STEM is used. Such deterioration hinders a clear electron beam image, resulting in difficulty in observation. Therefore, fabrication is required to remove a damaged layer if a thin sample piece is produced through the FIB fabrication. An inert gas ion beam with low acceleration is used to remove the damage layer.

However, since the thickness of the damage layer is approximately several nanometers, an engineer is required to have a high manipulation technique to remove the damaged layer.

CITATION LIST

Patent Literature

Patent Literature 1: JP Patent Publication (Kokai) No. 2007-193977 A

SUMMARY OF INVENTION

Technical Problem

Patent Literature 1 describes an example of an FIB fabrication device provided with an FIB optical system and a STEM optical system. This FIB fabrication device has been developed based on a combination of the FIB and the STEM techniques, and such a technique has been suggested that removes a damaged layer with a visual observation on a STEM image.

An object of the present invention is to provide a charged particle beam device and a sample production method capable of removing a damaged layer of a sample generated through an FIB fabrication sufficiently but at the minimum.

Solution To Problem

The charged particle beam device of the present invention includes a first element ion beam optical system unit which performs a first FIB fabrication to produce a sample piece from a sample, a second element ion beam optical system unit which removes a damaged layer formed on a surface of the sample piece, and a first element detector which detects a first element existing in the damaged layer.

A termination of the second FIB fabrication is determined if an amount of the first element existing in the damaged layer becomes smaller than a predefined threshold value.

Advantageous Effects of Invention

According to the present invention, it is possible to provide a charged particle beam device and a sample production method capable of removing a damaged layer of a sample generated through a fabrication by an FIB fabrication device sufficiently but at the minimum.

BRIEF DESCRIPTION OF DRAWINGS

FIG. 5 is a drawing illustrating a first embodiment of a method of removing the damaged layer using the charged particle beam device according to the present invention.

DESCRIPTION OF EMBODIMENTS

Figure 1:
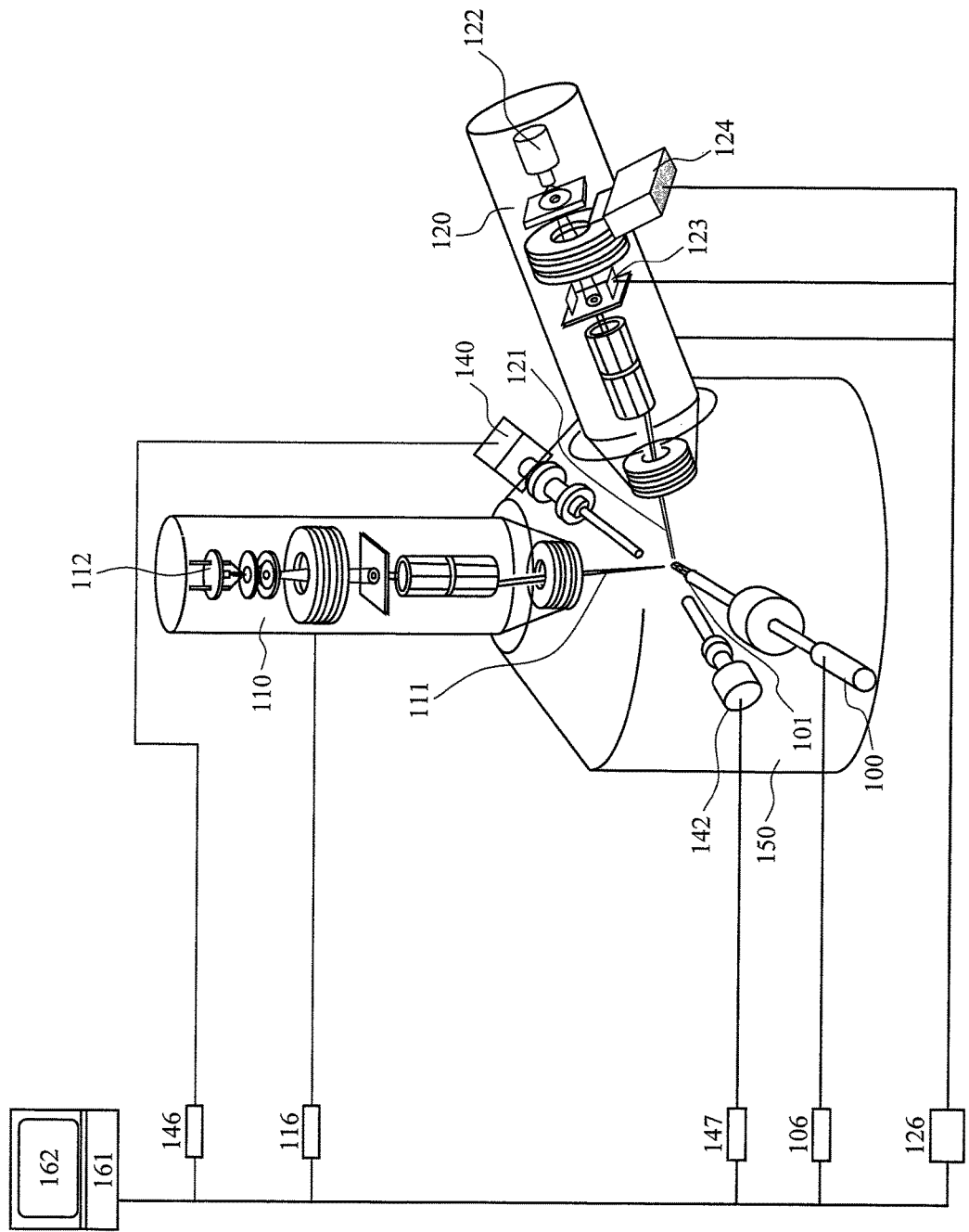
FIG. 1 is a schematic drawing of a first embodiment of a charged particle beam device according to the present invention.

FIG. 1 illustrates a first embodiment of the structure of the charged particle beam device according to the present invention. The charged particle beam device of this embodiment includes a movable sample stage 100 on which a sample 101 is placed; a first element ion beam optical system unit 110 for performing a first FIB fabrication by irradiating the sample 101 with a first element ion beam 111; a second element ion beam optical system unit 120 for performing a second FIB fabrication by irradiating the sample 101 with a second element ion beam 121; a secondary electron detector 142 for detecting a secondary electron generated from the sample 101; and a first element detector 140 for detecting the first element existing in the sample 101.

The sample stage 100, the first element ion beam optical system unit 110, the second element ion beam optical system unit 120, the first element detector 140, and the secondary electron detector 142 are disposed in a vacuum chamber 150.

The first element ion beam optical system unit 110 includes a first element ion source 112 for generating first element ions. A liquid metal ion source is used for the first element ion source 112, for example. This is because the liquid metal ion source is excellent in convergence and fabrication performance of ions. Gallium is used as the first element, for example. The energy of the first element ion is relatively high, and it may be defined at 30 to 40 kilovolts.

The second element ion beam optical system unit 120 includes a second element ion source 122 for generating second element ions, a closure mechanism 123 of a GUN valve, and a blanker 124 for blanking. An inert gas ion source having a greater particle size is used for the second element ion source 122. The second element may include argon or xenon, or the like, for example. Energy of the second element ion may be defined at a relatively low level, such as 1 kV or less.

The first element detector 140 may have any structure as far as the detector can detect the first element existing in the sample 101, and may be an ion detector, for example. A secondary ion mass spectrometry (referred to as a "SIMS", hereinafter) unit may be preferably applicable to the ion detector. The secondary ion mass spectrometry unit includes a mass spectrometry section and an ion detecting section. An example of the ion detector may include a magnetic sector detector, a quadrupole detector and a time-of-flight detector, or a combination thereof, and these detectors have mass spectrometry sections different from one another. According to the present invention, the ion detector may have a structure of any one of these types.

The charged particle beam device further includes a sample-position controller 106 for controlling a position of the sample stage 100 so as to determine a position to observe and fabricate the sample 101; a first-element-ion-beam-optical-system controller 116 for controlling the first element ion beam optical system unit 110; a secondary-electron-detector controller 147 for controlling the secondary electron detector 142; a first-element-detector controller 146 for controlling the first element detector 140; a second-element-ion-beam-optical-system controller 126 for controlling the second element ion beam optical system unit 120, the closure mechanism 123 and the blanker 124; a computer including a central processing unit 161 for controlling the above controllers; and a display unit 162.

The central processing unit 161 calculates control data for the sample-position controller 106, the first-element-ion-beam-optical-system controller 116, the second-element-ion-beam-optical-system controller 126, the first-element-detector controller 146, and the secondary-electron-detector controller 147, and sends the calculated results to respective controllers. A personal computer or a workstation is generally used as the central processing unit 161.

Description will be provided on the outline of the method of preparing the thin sample piece for a transmission electron microscopic (TEM) observation or a scanning transmission electron microscopic (STEM) observation by means of the charged particle beam device according to this embodiment. The original sample is prepared into a thin sample piece through the first FIB fabrication using the first element ion beam optical system unit 110, and through the second FIB fabrication using the second element ion beam optical system unit 120.

In the first FIB fabrication, the thin sample piece is produced from the original sample by using the first element ion beam having relatively high energy. A damaged layer is formed on the surface of the thin sample piece prepared through the first FIB fabrication. This damaged layer is formed by the first element used in the first FIB fabrication entering the surface, and being distributed there. The damaged layer deteriorates the transmitting performance of an electron beam. Therefore, the damaged layer existing in the surface of the sample deteriorates the quality of the TEM image or the STEM image as well as the accuracy of the observation and the analysis. In order to remove such a damaged layer, the second FIB fabrication is carried out. In the second FIB fabrication, the second element ion beam having relatively low energy is used so as to remove the damaged layer on the surface of the thin sample piece.

Liquid metal is used as the first element in the first FIB fabrication, and gaseous ion such as argon or xenon is used as the second element in the second FIB fabrication. In the second FIB fabrication, if the liquid metal is used at a low acceleration level, more amount of the liquid metal is accumulated than the amount of the fabrication, so that the liquid metal adheres to the sample. Meanwhile, the use of the beam of gaseous ion such as argon or xenon never contaminates the sample even at a low acceleration voltage.

In the second FIB fabrication, only the damaged layer should be removed, and it is not preferable to remove a portion below the damaged layer. The first element embedded in the surface of the thin sample piece is observed by using the first element detector 140. If the amount of the first element becomes small, it is determined that the damaged layer is removed, and the second FIB fabrication is determined to be terminated.

An oxygen ion beam may be used as the second element ion beam. The oxygen ion beam has a high ionization efficiency, so that more first element ions can be detected. Accordingly, this enables a highly precise detection and removal of the damaged layer. A cluster ion beam may be used as the second element ion beam. The cluster ion beam has a smaller depth of the ion entry, compared to that of a single atomic ion beam; thus it is possible to avoid damaged layer formation through the second FIB fabrication. Accordingly, the damaged layer can be removed even at the lower acceleration voltage without decreasing the fabrication speed.

An unfocused broad ion beam may be used as the second element ion beam. In this case, the second element ion beam optical system unit 120 and the second-element-ion-beam-optical-system controller 126 for controlling this second element ion beam optical system unit 120 may be made in a compact size with inexpensive cost.

An auxiliary FIB fabrication using an element ion beam other than the second element may be performed between the first and the second FIB fabrications. In this auxiliary FIB fabrication, an ion beam at a low acceleration voltage of approximately 1 kV to 5 kV may be used, for example. The fabrication speed is smaller in the auxiliary FIB fabrication in order to preliminarily remove the damaged layer. Hence, it takes more time to complete the removal. On the other hand, the thickness of the damaged layer is reduced through the auxiliary FIB fabrication, so that the second FIB fabrication is completed in a shorter time.

Figure 2A:
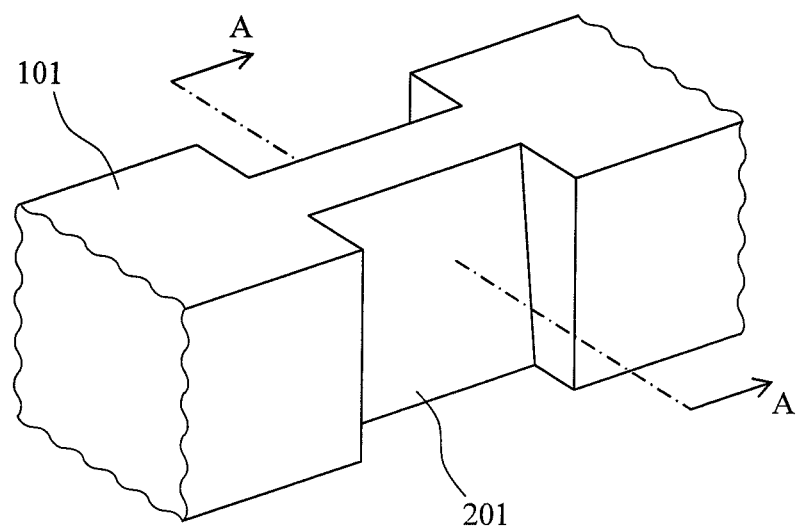
FIG. 2A is a drawing explaining an example of a thin sample piece for a transmission electron microscopic (TEM) observation or a scanning transmission electron microscopic (STEM) observation.
Figure 2B:
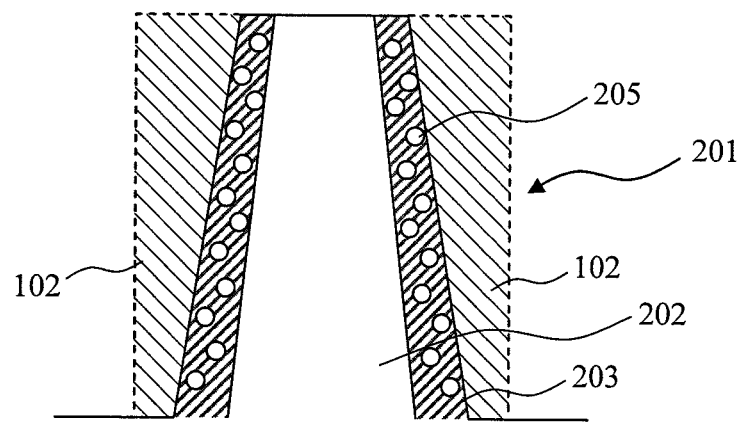
FIG. 2B is a drawing explaining damaged layers formed on the thin sample piece.
Figure 2C:
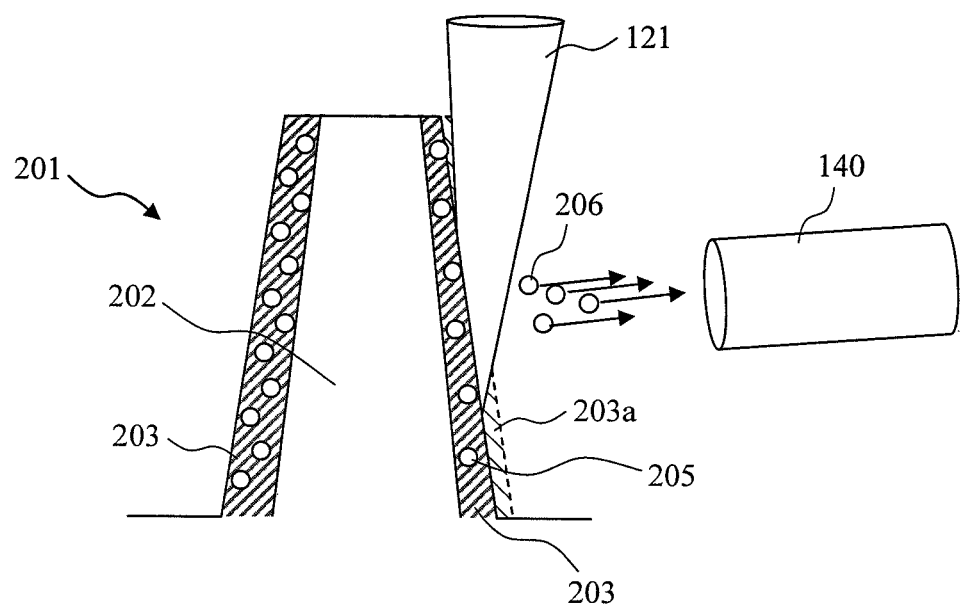
FIG. 2C is a drawing explaining a method of removing the damaged layers formed on the thin sample piece.

With reference to FIG. 2A, FIG. 2B and FIG. 2C, description will be now provided on an example of a thin sample piece for a transmission electron microscopic (TEM) observation or a scanning transmission electron microscopic (STEM) observation. FIG. 2A illustrates an example of the sample 101 supported on the sample stage 100. The thin sample piece 201 is prepared by performing the first fabrication for the sample 101 using the first element ion beam optical system unit 110.

FIG. 2B is a cross sectional view taken along line A-A of FIG. 2A. An area 102 indicated by oblique lines is a portion of the sample removed through the first FIB fabrication. The damaged layer 203 is formed in the vicinity of the surface of the thin sample piece 201. The first element 205 used in the first FIB fabrication has entered and has been distributed in the damaged layer 203. In this case, gallium is used as the first element 205; thus gallium is embedded in the damaged layer 203.

The thickness of the damaged layer 203 is approximately 30 to 40 nanometers, for example. There is a portion 202 that is not damaged more inward than the damaged layer 203. The second FIB fabrication is performed so as to remove the damaged layer 203.

With reference to FIG. 2C, the second FIB fabrication will be described. The thin sample piece 201 is irradiated with the second element ion beam 121 by using the second element ion beam optical system unit 120, so as to remove the damaged layer 203. A region 203a indicated by oblique lines is a removed portion through the second FIB fabrication. As described above, in order to avoid the damaged layer production due to the second element, the energy of the second element ion beam may be defined at 1 kV or less in the second FIB fabrication, for example. Argon or xenon may be used as the second element.

In the second FIB fabrication, it is necessary to remove only the damaged layer 203, but to avoid the removal of the internal portion 202. For this reason, the first element 205 embedded in the surface of the thin sample piece is observed by using the first element detector 140. In the second FIB fabrication, when the damaged layer 203 is irradiated with the second element ion beam 121, the first element ions 206 are emitted as the secondary ions. Specifically, the first element 205 in the damaged layer 203 is forced out. These first element ions 206 are detected on the first element detector 140. In this embodiment, the second FIB fabrication and the detection of the first element 205 are carried out at the same time through the irradiation of the second element ion beam 121. The first element detector 140 is an ion detector for detecting gallium that is the first element ion 206.

Figure 3A:
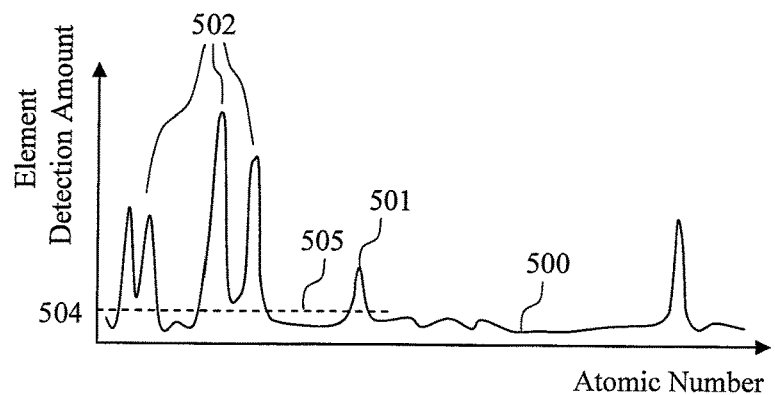
FIG. 3A is a drawing illustrating an example of element spectra detected on a first element detector of the charged particle beam device according to the present invention.

FIG. 3A illustrates an example of a curve 500 representing element spectra detected on the first element detector 140. The horizontal axis represents atomic numbers, and the vertical axis represents detection amounts of elements. Element peaks 502 other than the peak 501 of gallium also appear in the curve 500. In this example, the content of gallium in the damaged layer is measured. When the damaged layer is removed through the second FIB fabrication, the peak 501 of gallium becomes gradually smaller. A line 505 denoting a threshold value 504 is indicated in the curve 500. When the peak 501 of gallium becomes smaller than the line 505, it may be determined that the damaged layer is removed. The central processing unit 161 analyzes an output signal from the first element detector 140, and determines the termination of the second FIB fabrication when the peak 501 of gallium becomes smaller than the line 505.

This threshold value 504 and the line 505 can be input numerically on the screen of the display unit 162. Therefore, only the damaged layer in the target area of the second FIB fabrication can be removed by setting the threshold value 504, and the removal of a lower layer under the damaged layer can be avoided. The curve 500 representing the element spectra is displayed on the display unit 162, so that an operator can check detection amounts of various elements. Even if gallium is detected in a region other than the damaged layer, this is nothing to do with the second FIB fabrication.

Figure 3B:
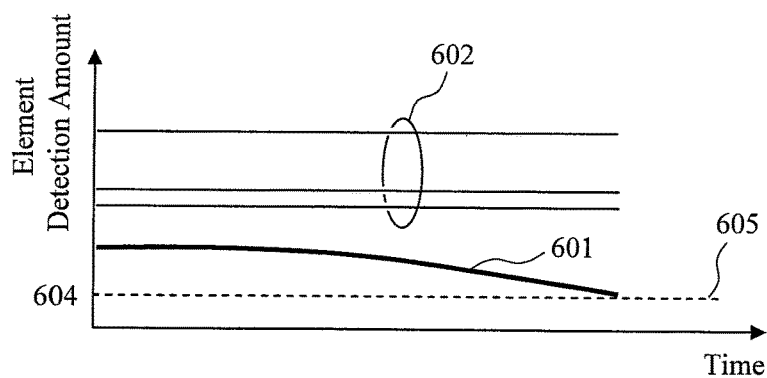
FIG. 3B is a drawing showing the time course of the change in peak value of the first element detected on the first element detector of the charged particle beam device according to the present invention.

FIG. 3B is a graph representing the time course of the change in peak value of the elements appearing in the element spectra in FIG. 3A. The horizontal axis represents the second FIB fabrication time, and the vertical axis represents the element detection amount. A graph 601 representing the peak value of gallium gradually descends in accordance with the time course of the second FIB fabrication. Peaks 602 of other elements indicate no change. A line 605 indicating a threshold value 604 is shown relative to the graph 601. When the peak 601 of gallium becomes smaller than the line 605, it can be determined that the removal of the damaged layer is completed. The central processing unit 161 determines the termination of the second FIB fabrication.

Figure 3C:
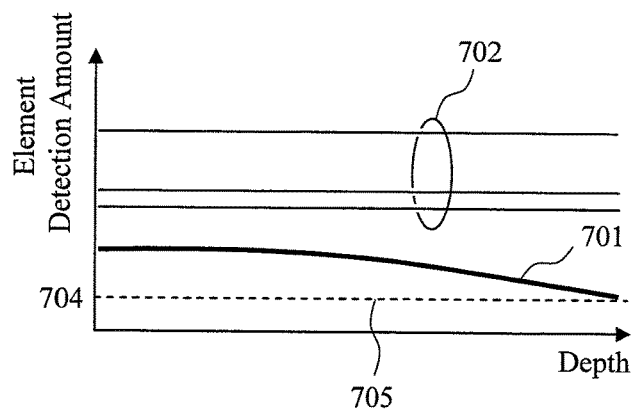
FIG. 3C is a drawing showing a relation between a depth of the thin sample piece and an attenuation of the peak value of the first element detected on the first element detector of the charged particle beam device according to the present invention.

FIG. 3C is a graph representing a relation between attenuations of the peak values of the elements appearing in the element spectra in FIG. 3A and the depths of the thin sample piece. The horizontal axis represents the depth of the thin sample piece, and the vertical axis represents the element detection amount. A graph 701 representing the peak value of gallium gradually descends in accordance with the depth of the thin sample piece. The depth of the thin sample piece represents a thickness of a layer removed from the damaged layer, and is corresponding to the second FIB fabrication time. Hence, the graph 701 has an approximately similar curve to the graph 601 of FIG. 3B. Peaks 702 of other elements indicate no change. A line 705 indicating a threshold value 704 is shown relative to the graph 701. When the peak 701 of gallium becomes smaller than the line 705, it can be determined that the removal of the damaged layer is completed. The central processing unit 161 determines the termination of the second FIB fabrication.

Figure 4:
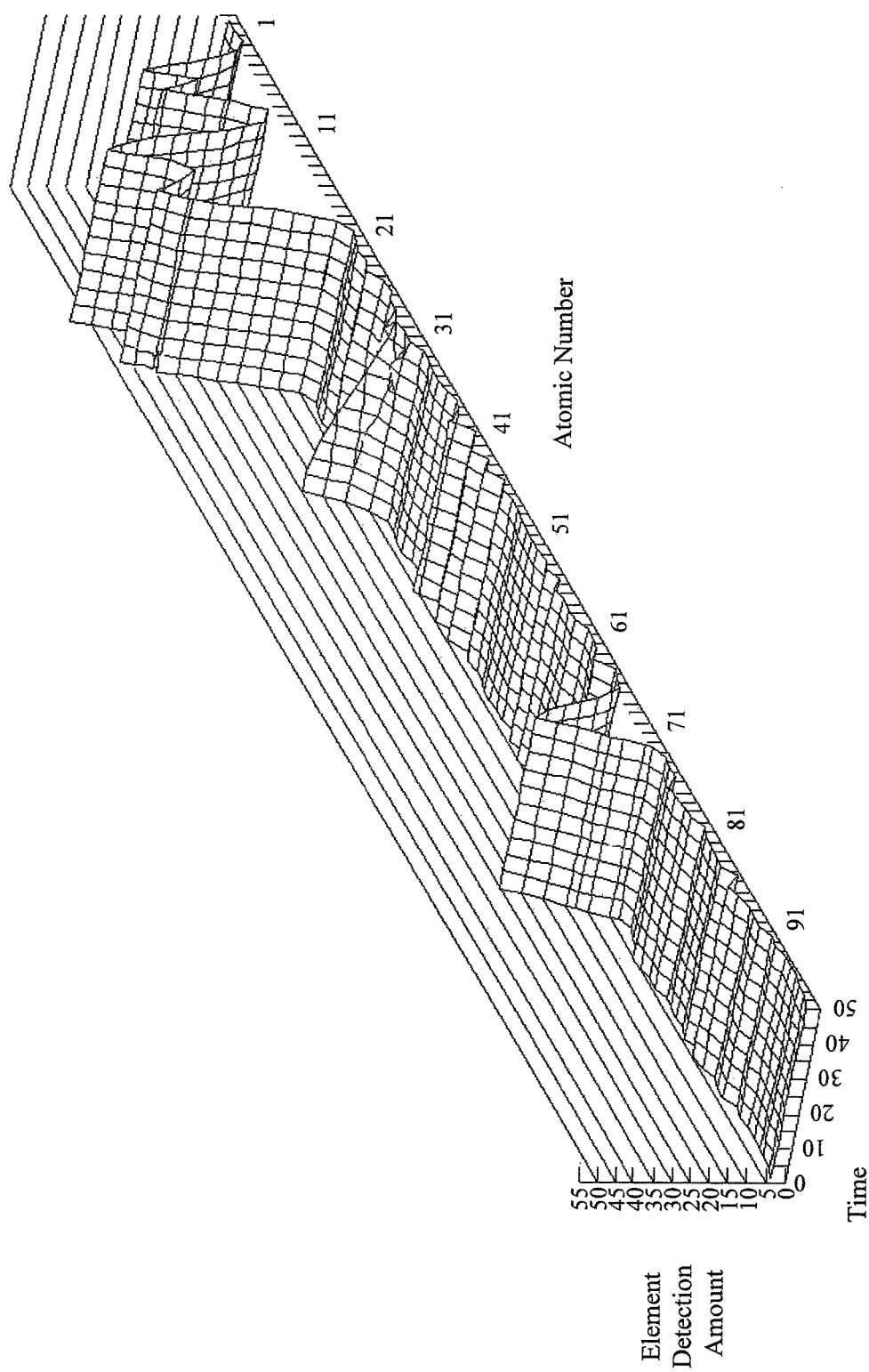
FIG. 4 is a drawing illustrating a three-dimensional display of detection amounts of elements detected on the first element detector of the charged particle beam device according to the present invention.

FIG. 4 is a 3D display representing synthesized data of FIG. 3A and FIG. 3B, the horizontal axis represents the element numbers and the second FIB fabrication time, and the vertical axis represents the detection amounts of the elements. It should be appreciated that gallium of the atomic number 31 is gradually attenuated over time. The graphs representing the change in element spectra shown in FIG. 3A, FIG. 3B, FIG. 3C, and FIG. 4 can be mutually changed over on the screen of the display unit 162. If the central processing unit 161 determines the termination of the second FIB fabrication, and the second FIB fabrication is completed in accordance with an instruction from the central processing unit 161, it may be unnecessary to display these graphs representing the change in element spectra on the display unit 162. If the central processing unit 161 determines the termination of the second FIB fabrication, and the operator terminates the second FIB fabrication, it is necessary to display these graphs on the display unit 162.

With reference to FIG. 5, description will now be provided on the first embodiment of the procedure in the method of fabricating the thin sample piece by using the charged particle beam device according to the present invention. In this embodiment, gallium is used as the first element, argon is used as the second element, and a quadrupole ion detector is used as the first element detector.

In Step S101, the operator produces the thin sample piece 201 as illustrated in FIG. 2A through the first FIB fabrication. Specifically, the sample is irradiated with a gallium ion beam by using the first element ion beam optical system unit 110, so as to prepare the thin sample piece. The damaged layer with a depth of several tens of nanometers is formed on the surface of this thin sample piece.

In Step S102, the position adjustment of the second FIB fabrication is carried out. Specifically, the irradiation position of the argon ion beam is so adjusted as to align with the fabrication position of the thin sample piece. The operator monitors the screen displayed on the display unit 162, and controls the sample-position controller 106 through the central processing unit 161, so as to adjust the position of the sample supported on the sample stage 100. The fabrication position of the thin sample piece is adjusted based on the fabricating marks of the argon ion beam, the secondary electron images formed by the gallium ion beam, and the positional relationship between the sample stage and the sample.

In Step S103, the second FIB fabrication is started. The operator starts the operation of the second FIB fabrication through the central processing unit 161, and controls the position of the sample stage 100 through the sample-position controller 106. Then, the thin sample piece is irradiated with the argon ion beam to remove the damaged layer by using the second element ion beam optical system unit 120.

In Step S104, at the same time of starting the second FIB fabrication, the first element distributed in the damaged layer is detected on the first element detector. The first element detector may be a detector capable of detecting elements other than the first element, but preferably is configured to be dedicated to the detection of the first element. In this embodiment, the ion detector detects gallium distributed in the damaged layer. The ion detector may be an ion detector dedicated to the detection of gallium, and thereby realizing size reduction and cost reduction of the charged particle beam device.

In Step S105, the detection amounts of the various elements detected on the first element detector are displayed on the display unit 162, as shown in FIG. 3A. The operator can monitor the detection amounts of the various elements on the display unit 162.

In Step S106, the first element is compared to a predefined threshold value. Specifically, the value of the peak 501 of gallium in the spectrum 500 is compared to the predefined threshold value 504. If the peak 501 of gallium becomes smaller than the threshold value 504, the process proceeds to Step S107. If the peak 501 of gallium is greater than the threshold value 504, the process returns to Step S103, and the removal of the damaged layer through the second FIB fabrication is continued. The above processing in Step S106 may be carried out by the central processing unit 161, or may be carried out by the operator, instead.

In Step S107, the second FIB fabrication is terminated. The second FIB fabrication may be automatically terminated by the central processing unit 161, or the operator may send an instruction to the central processing unit 161 through the input unit, instead. The central processing unit 161 controls not to irradiate the thin sample piece with the argon ion beam. For example, the blanker 124 may be controlled to deflect the argon ion beam by using the second-element-ion-beam-optical-system controller 126. The closure mechanism 123 of the GUN valve may be controlled to stop the argon ion beam by using the second-element-ion-beam-optical-system controller 126. The acceleration voltage of the argon ion source may be lowered by the second-element-ion-beam-optical-system controller 126. The sample-position controller 106 may be activated so as to move the thin sample piece out of the irradiation region of the argon ion beam. In such a manner, it is possible to avoid the irradiation of the argon ion beam onto the thin sample piece. A plurality of the above control operations may be used in combination.

The steps of the fabrication process of the thin sample piece as illustrated in FIG. 5 are completed. A screen for selecting the subsequent operation may be displayed on the display unit 162. As the subsequent operation, the damaged layer removal flow may be repeated again using a different threshold value or the operation may be terminated. If the operator selects the former operation, the process returns to Step S103 to start the second FIB fabrication; and if the operator selects the latter operation, the process is terminated.

Figure 6A:
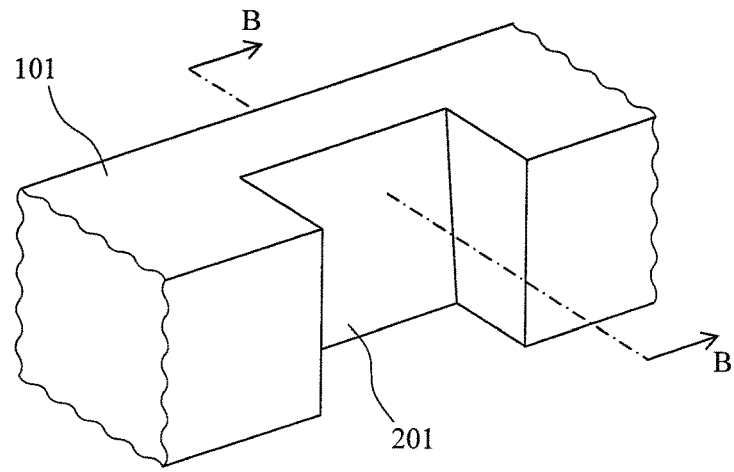
FIG. 6A is a drawing explaining an example of the sample for a scanning electron microscopic (SEM) observation.
Figure 6B:
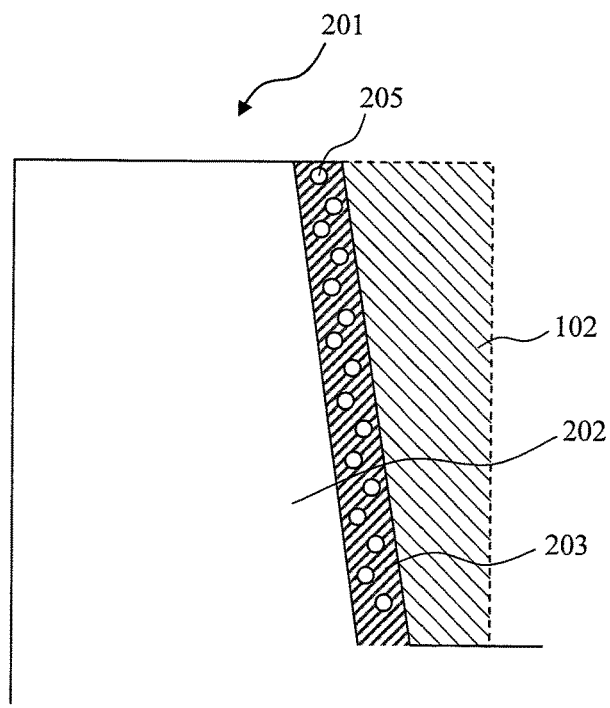
FIG. 6B is a drawing explaining the damaged layer formed on the sample for a scanning electron microscopic (SEM) observation.

With reference to FIG. 6A and FIG. 6B, an example of the sample for a scanning electron microscopic (SEM) observation will be described. FIG. 6A illustrates an example of the sample 101 supported on the sample stage 100. The first FIB fabrication is performed on the sample 101 by using the first element ion beam optical system unit 110, so as to produce the sample 201.

FIG. 6B is a cross sectional view taken along line B-B of FIG. 6A. The region 102 indicated by oblique lines is a portion removed through the first FIB fabrication. The damaged layer 203 is formed in the vicinity of the surface of the thin sample piece 201. The first element 205 used in the first FIB fabrication has entered the damaged layer 203, and has been distributed there. In this case, gallium is used as the first element 205; thus gallium is embedded in the damaged layer 203.

The scanning electron microscope irradiates the surface of the sample with an electron beam, and detects generated secondary electrons, and images the electrons. Hence, no electron beam is needed to be transmitted through the sample. The sample is unnecessary to be prepared into a thin piece. As illustrated in FIG. 6B, only one surface of the original sample is fabricated in the first FIB fabrication. A damaged layer 203 is also formed on a fabricated surface of the sample 201 produced even in such a manner. Therefore, this damaged layer 203 should be removed. In this embodiment, since the damaged layer 203 is removed through the second FIB fabrication, a SEM photograph in a preferable quality can be obtained in the scanning electron microscopic observation, and thereby enhancing accuracy of the analyses. The present invention is applicable to a preparation of a sample for a SEM observation.

In the above described first embodiment of the present invention, the ion detector is used for detecting the first element embedded in the damaged layer 203. In the following second embodiment of the present invention, in order to detect the first element embedded in the damaged layer 203, irradiation of an electron beam is performed, and X rays generated by this irradiation are detected.

Figure 7:
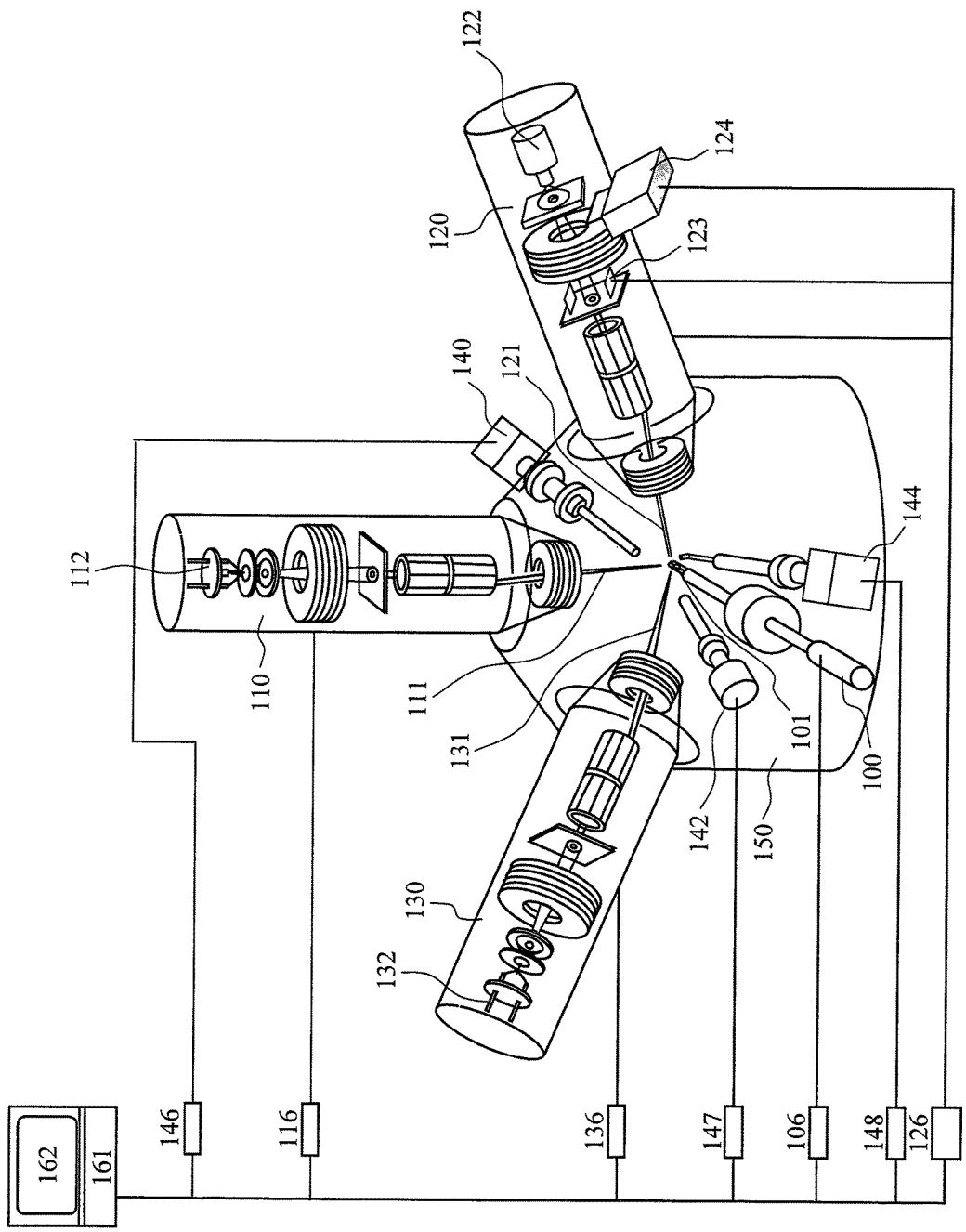
FIG. 7 is a schematic drawing of a seventh embodiment of the charged particle beam device of the present invention.

With reference to FIG. 7, description will now be provided on the second embodiment of the charged particle beam device of the present invention. Compared to the charged particle beam device of the first embodiment of FIG. 1, the following point is different from the first embodiment: the charged particle beam device of this embodiment additionally includes an electron beam optical system unit 130 having an electron source 132, an electron-beam-optical-system controller 136, a deposition gas supply unit 144, and a deposition gas supply controller 148. In addition, the charged particle beam device of this embodiment uses an X ray detector as the first element detector 140.

The central processing unit 161 calculates control data for the sample-position controller 106, the first-element-ion-beam-optical-system controller 116, the second-element-ion-beam-optical-system controller 126, the electron-beam-optical-system controller 136, the first-element-detector controller 146, the secondary-electron-detector controller 147, and the deposition gas supply controller 148, and sends calculated results to the respective controllers.

Compared to the first embodiment of FIG. 1, the method of detecting the first element in the charged particle beam device of this embodiment is different from that of the first embodiment. In this embodiment, the first element is detected by the electron beam optical system unit 130, and the first element detector 140, that is, the X ray detector. The electron beam optical system unit 130 irradiates the thin sample piece with an electron beam 131. X rays generated from the thin sample piece are detected by the X-ray detector. An output of the X-ray detector is analyzed to detect the first element included in the damaged layer 203.

Figure 8:
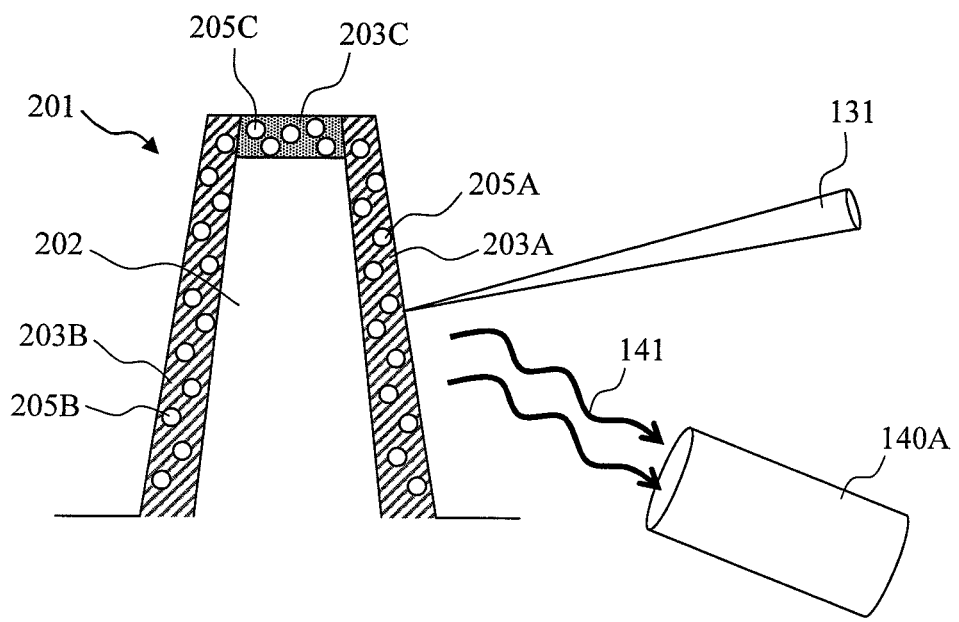
FIG. 8 is a drawing explaining a method of removing the damaged layers formed on the thin sample piece.

With reference to FIG. 8, description will now be provided on an example of the thin sample piece for a transmission electron microscopic (TEM) observation or a scanning transmission electron microscopic (STEM) observation. In this embodiment, gallium is used as the first element, argon is used as the second element, and the X-ray detector is used as the first element detector. The thin sample piece 201 in the drawing is prepared through the first FIB fabrication, and damaged layers 203A and 203B are formed on its both sides. A protection film 203C is formed on the top surface of the thin sample piece 201. The protection film 203C is so provided as to protect wiring patterns formed on the surface of the sample 102, and is formed prior to the first FIB fabrication. The protection film 203C is formed by using a deposition gas, and an ion beam or an electron beam. The first element ion beam may be used to form the protection film 203C in the viewpoint of the accumulation speed and accuracy of the position definition. In this case, the first element 205C is contained in the protection film 203C.

In this embodiment, the damaged layer is also removed through the second FIB fabrication, that is, by using the second element ion beam. In this embodiment, the second element ion beam is an argon ion beam. In this embodiment, since the first element 205C is contained in the protection film 203C, an accurate detection of the first elements 205A and 205B in the damaged layers 203A and 203B may not be conducted by the method of the first embodiment as illustrated in FIG. 2C. Specifically, in the first embodiment, the second FIB fabrication and the detection of the first element 205 are carried out at the same time through the irradiation of the second element ion beam 121. When the damaged layer in the vicinity of the protection film 203C is fabricated through the second FIB fabrication, not only the first elements 205A and 205B contained in the damaged layer but also the first element 205C contained in the protection film 203C may be detected.

For this reason, in this embodiment, the damaged layer 203A on one side of the thin sample piece 201 is irradiated with the electron beam 131. The electron beam 131 has a smaller irradiating area, so that the beam can irradiate only the damaged layer 203A without irradiating the protection film 203C. Accordingly, it is possible to eliminate a possibility to detect the first element 205C contained in the protection film 203C.

In this embodiment, the damaged layers 203A and 203B on the both sides of the thin sample piece 201 are removed by turns with the second element ion beam. If the thin sample piece having a thickness of approximately 100 nanometers is irradiated with the electron beam, X rays are generated from all the elements on the irradiating straight line. This means that characteristic X rays 141 are generated from the both sides of the thin sample piece 201. Hence, the X-ray detector 140A measures the first ion elements 205A and 205B existing in the damaged layers 203A and 203B on the both sides at the same time. To the contrary, in the case of removing only the damaged layer 203A, the speed of reduction of the first element 205 detected on the X-ray detector 140A becomes smaller. Consequently, it cannot be properly determined when the second FIB fabrication should be terminated.

Figure 9:
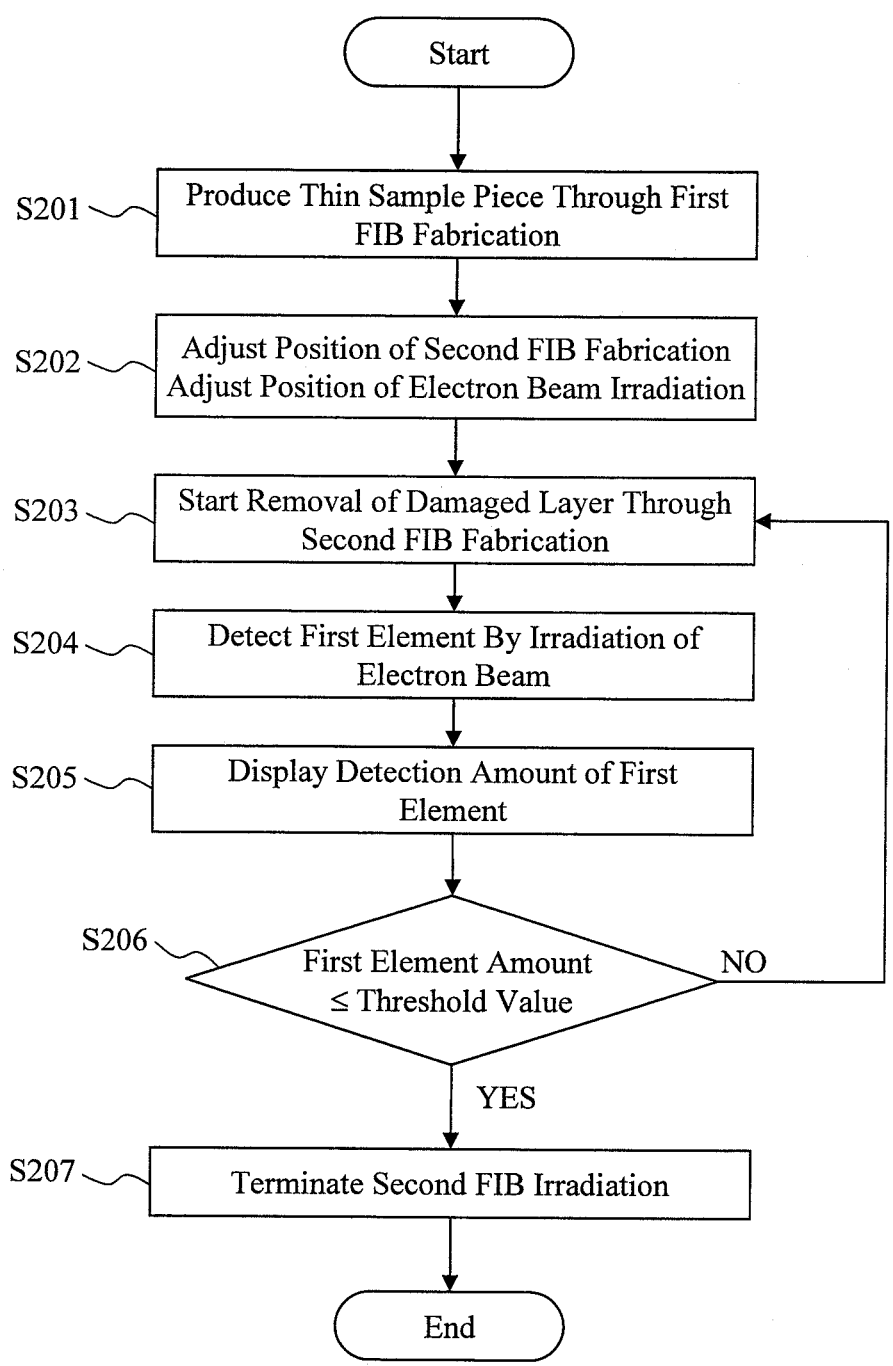
FIG. 9 is a drawing illustrating a second embodiment of the method of removing the damaged layer using the charged particle beam device according to the present invention.

With reference to FIG. 9, description will be provided on the second embodiment of the method of fabricating the thin sample piece using the charged particle beam device according to the present invention. In this embodiment, gallium is used as the first element, argon is used as the second element, and the X-ray detector is used as the first element detector.

In Step S201, the operator prepares the thin sample piece 201 through the first FIB fabrication, as illustrated in FIG. 3A. Specifically, the thin sample piece is prepared by irradiating the sample with the gallium ion beam using the first element ion beam optical system unit 110. The damaged layer having a depth of several tens of nanometers is formed on the surface of this thin sample piece. In addition, this thin sample piece has the protection film 203C.

In Step S202, the second FIB fabrication position and the electron beam irradiation position are adjusted. The method of adjusting the position of the second FIB fabrication has been described in Step S102 of the first embodiment in FIG.

5. The adjustment of the irradiation position of the electron beam is carried out in the same manner as that of adjusting the position of the second FIB fabrication. Specifically, the operator monitors the screen displayed on the display unit 162, and controls the electron-beam-optical-system controller 136 through the central processing unit 161, so as to adjust the position of the sample supported on the sample stage 100.

The position of the second FIB fabrication and the position of the electron beam irradiation may be placed on the same surface of the thin sample piece, and is not necessarily placed at the same position. This configuration reduces the number of operations for rotation and planar movement of the sample stage.

In Step S203, the second FIB fabrication is started. In this embodiment, the damaged layers 203A and 203B on the both sides of the thin sample piece 201 are removed by turns. Specifically, using the argon ion beam, the damaged layer 203A on the surface which is irradiated with the electron beam, and the damaged layer 203B on the opposite surface are fabricated by turns in the same manner.

In Step S204, the thin sample piece is irradiated with the electron beam, and the characteristic X rays generated from the thin sample piece are detected on the X-ray detector. The output of the X-ray detector is analyzed so as to detect gallium distributed in the damaged layers. Every element has its unique X-ray spectrum, so that it is possible to find the amount of gallium based on the peak height of the spectrum of gallium through the detection of X rays. In this embodiment, an elemental mapping image can be displayed on the display unit 162.

Step S205 to Step S207 are the same as Step S105 to Step S107 of the first embodiment of FIG. 5.

Figure 10A:
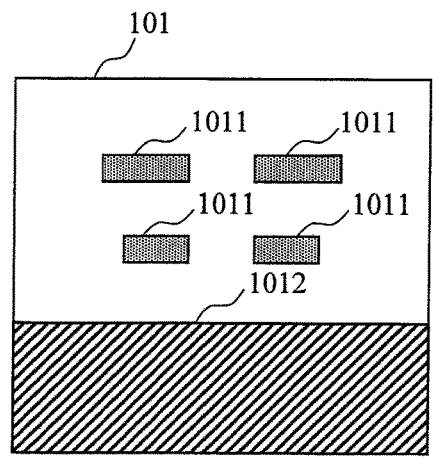
FIG. 10A is a drawing illustrating a secondary electron image of the thin sample piece prepared through the first FIB fabrication using the charged particle beam device of the present invention.
Figure 10B:
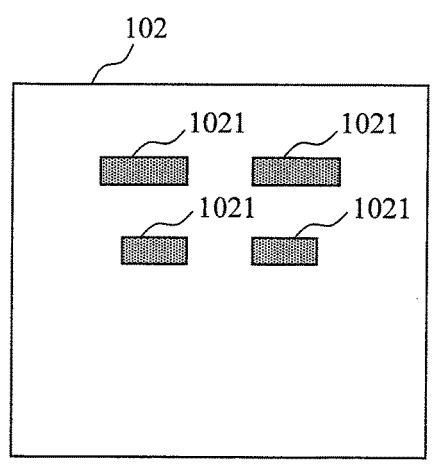
FIG. 10B is a drawing illustrating an example of an image obtained through an elemental mapping of elements included in a material constituting the thin sample piece.
Figure 10C:
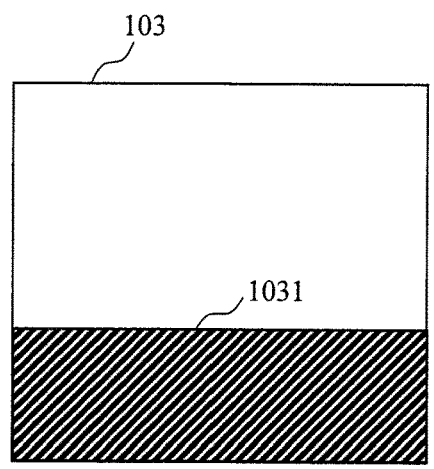
FIG. 10C is a drawing illustrating an example of an image obtained through the elemental mapping of the elements included in the material constituting the thin sample piece.

Description will be provided with reference to FIG. 10A, FIG. 10B, and FIG. 10C. FIG. 10A illustrates a secondary electron image 101 of the thin sample piece prepared through the first FIB fabrication. The secondary electron image 101 can be obtained by analyzing the output of the secondary electron detector 142. In this secondary electron image 101, particular regions 1011, and 1012 have a different brightness from a brightness in the surroundings. Wiring patterns are formed in these regions 1011, and 1012, and have a different material from a material in the surroundings.

An image 102 as illustrated in FIG. 10B is obtained through the elemental mapping of elements included in materials constituting the region 1011 of the secondary electron image 102. An image 103 as illustrated in FIG. 10C is obtained through the elemental mapping of elements included in materials constituting the region 1012 of the secondary electron image 102. These images 101, 102 and 103 are displayed on the display unit 162. The elemental mapping is well-known to those skilled in the art, in which, based on the element spectra illustrated in FIG. 3A, peaks of predefined elements are digitized and displayed two-dimensionally.

Figure 11A:
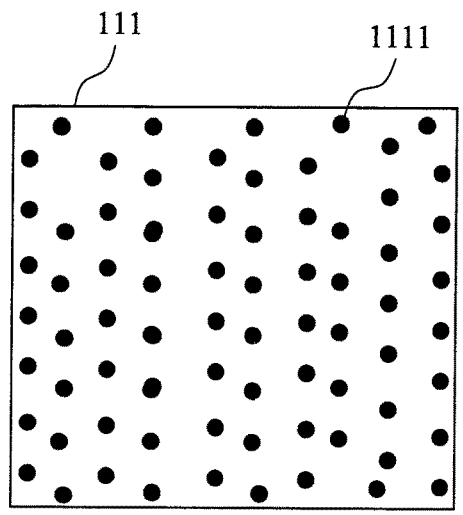
FIG. 11A is a drawing illustrating an example of an image obtained through the elemental mapping of the first element included in the damaged layer of the thin sample piece.
Figure 11B:
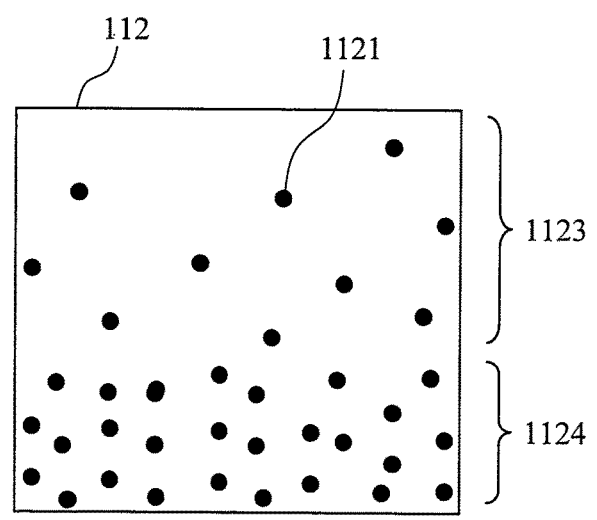
FIG. 11B is a drawing illustrating an example of an image obtained through the elemental mapping of the first element included in the damaged layer of the thin sample piece.

Description will be provided with reference to FIG. 11A and FIG. 11B. Images 111 and 112 illustrated in FIG. 11A and FIG. 11B, respectively, are obtained through the elemental mapping of gallium that is the first element using the secondary electron image 101 of FIG. 10A. Regions 1111 and 1112 of black spots in these images 111 and 112 indicate gallium as the first element. These images 111 and 112 are displayed on the display unit 162.

In the image 111 illustrated in FIG. 11A, the regions 1111 indicating gallium are uniformly distributed. After the second FIB fabrication is carried out and the damaged layers are further removed, the number or the area of the regions 1111 indicating gallium becomes smaller. If the regions 1111 become smaller than a predefined value, it is determined that the damaged layers are removed sufficiently. The operator may determine the termination of the second FIB fabrication while monitoring the image 111. If the regions representing the amount of the first element per unit area in the image 111 become smaller than a predefined threshold value, the central processing unit 161 may determine the termination of the second FIB fabrication, and the second FIB fabrication may further be automatically terminated.

In the image 112 illustrated in FIG. 11B, less regions 1112 representing gallium are distributed in the upper half part 1123, and more regions 1112 representing gallium are distributed in the lower half part 1124. This indicates an uneven removal of the damaged layer through the second FIB fabrication, in which more damaged layer was removed in the upper half part, and less damaged layer was removed in the lower half part. The operator monitors the image 112, and corrects the inclination and the fabrication position of the thin sample piece.

According to the present invention, it is possible to accurately determine the timing to terminate the removal of the damaged layer, and thereby attaining efficient removal of the damaged layer of not only a thin sample piece of an existing material and having an existing structure but also a thin sample piece of a new material and having a new structure, without relying on an operator's experienced skill. In a failure analysis using a TEM or a STEM, a thin sample piece whose damaged layer is sufficiently removed is used, so that it is possible to obtain an image in a good quality. Accordingly, enhancement of accuracy of the structure observation and the element analysis can be realized, and thereby contributing to enhancement of the technique of the failure analysis and the structural analysis.

The embodiments of the present invention has been described above, but it should be easily appreciated by those skilled in the art that the present invention is not limited to the above description, and various alternations may be made within the scope of the present invention as set forth in the claims.

REFERENCE SIGNS LIST

100 Sample stage; 101 Sample; 106 Sample-position controller; 110 First element ion beam optical system unit; 111 First element ion beam; 112 First element ion source; 116 First-element-ion-beam-optical-system controller; 120 Second element ion beam optical system unit; 121 Second element ion beam; 122 Second element ion source; 123 Closure mechanism; 124 Blanker; 126 Second-element-ion-beam-optical-system controller; 130 Electron-beam-optical-system unit; 131 Electron beam; 132 Electron source; 136 Electron-beam-optical-system controller; 140 First element detector; 140A X-ray detector; 142 Secondary electron detector; 144 Deposition gas supply unit; 146 First-element-detector controller; 147 Secondary-electron-detector controller; 148 Deposition gas supply controller; 150 Vacuum chamber; 161 Central processing unit; 162 Display unit; 201 Thin sample piece; 202 Internal portion; 203, 203A, 203B Damaged layer; 203C Protection film; 205, 205A, 205B, 205C First element; 206 First element ion.

The invention claimed is:
1. A charged particle beam device comprising:
a sample stage which supports a sample;
a first element ion beam optical system unit;

a sample piece formed from the sample by irradiating the sample with a first element ion beam during a first FIB fabrication;
a second element ion beam optical system unit;
a removed damage layer on a surface of the sample piece from irradiating the sample piece with a second element ion beam during the second FIB fabrication;
a secondary ion mass spectrometry unit;
a simultaneous detection of an amount of a first element from the first element ion beam existing in the removed damaged layer and the second FIB fabrication by the secondary ion mass spectrometry unit;
a fabrication terminator which terminates the second FIB fabrication as a result of the amount of the first element from the first element ion beam existing in the removed damaged layer detected by the secondary ion mass spectrometry being less than a predefined threshold value for the first element existing in the removed damaged layer; and
a comparison unit comprising a processor which controls the fabrication terminator and instructs the fabrication terminator to terminate the second FIB fabrication as a result of the amount of the first element from the first element ion beam existing in the removed damaged layer being less than a predefined threshold value for the first element existing in the removed damaged layer.

2. The charged particle beam device according to claim 1, wherein
the secondary ion mass spectrometry unit comprises any ion detector of a magnetic sector detector, a quadrupole detector, a time-of-flight detector, and a combination of the detectors.

3. The charged particle beam device according to claim 1, wherein
the first element is gallium, and
the first element detector is configured to detect only gallium.

4. The charged particle beam device according to claim 1, wherein
the second element is argon.

5. The charged particle beam device according to claim 1, wherein
the charged particle beam device is configured to produce an elemental mapping image that displays distributions of the first element as a two-dimensional image, based on spectra of amounts of elements obtained by the first element detector.

6. The charged particle beam device according to claim 5, wherein
the charged particle beam device is configured to determine the termination of the second FIB fabrication based on the distributions of the first element represented in the elemental mapping image.

7. A charged particle beam device comprising:
a sample stage which supports a sample;
a first element ion beam optical system unit;
a sample piece formed from the sample by irradiating the sample with a first element ion beam during a first FIB fabrication;
a second element ion beam optical system unit;
a removed damage layer on a surface of the sample piece from irradiating the sample piece with a second element ion beam during the second FIB fabrication;
an electron beam optical system unit;
a simultaneous detection of an amount of a first element from the first element ion beam existing in the removed damaged layer with the second FIB fabrication by the electron beam optical system unit;
an irradiated sample piece which is irradiated by an electron beam of the electron beam optical system unit;
an X-ray detector which detects X rays from the sample piece;
a fabrication terminator which terminates the second FIB fabrication as a result of the amount of the first element from the first element ion beam existing in the removed damaged layer detected by the X-ray detector being less than a predefined threshold value for the first element existing in the removed damaged layer; and
a comparison unit comprising a processor which controls the fabrication terminator and instructs the fabrication terminator to terminate the second FIB fabrication as a result of the amount of the first element from the first element ion beam existing in the removed damaged layer analyzed by an output from the X-ray detector being less than a predefined threshold value for the first element existing in the removed damaged layer.

8. The charged particle beam device according to claim 1, wherein
the fabrication terminator is a blanker.

9. The charged particle beam device according to claim 1, wherein
the fabrication terminator is a closure mechanism of the valve of second element ion beam optical system unit.

10. The charged particle beam device according to claim 1, wherein
the fabrication terminator is a second element ion beam optical system controller.

11. The charged particle beam device according to claim 1, wherein
the fabrication terminator is a sample position controller.

12. The charged particle beam device according to claim 7, wherein
the fabrication terminator is a blanker.

13. The charged particle beam device according to claim 7, wherein
the fabrication terminator is a closure mechanism of the valve of second element ion beam optical system unit.

14. The charged particle beam device according to claim 7, wherein
the fabrication terminator is a second element ion beam optical system controller.

15. The charged particle beam device according to claim 7, wherein
the fabrication terminator is a sample position controller.

16. A charged particle beam device comprising:
a sample stage which supports a sample;
a first element ion beam optical system unit which performs a first FIB fabrication to form a sample piece from the sample by irradiating the sample with a first element ion beam;
a second element ion beam optical system unit which performs a second FIB fabrication to remove a damaged layer formed on a surface of the sample piece by irradiating the sample piece with a second element ion beam;
a secondary ion mass spectrometry unit which detects an amount of a first element from the first element ion beam existing in the damaged layer simultaneously with the second FIB fabrication;
an interface receiving a threshold value for the amount of the first element from the first element ion beam existing in the damaged layer;

a fabrication terminator which terminates the second FIB fabrication as a result of the amount of the first element from the first element ion beam existing in the damaged layer detected by the secondary ion mass spectrometry being less than the threshold value; and a comparison unit comprising a processor which controls the fabrication terminator and instructs the fabrication terminator to terminate the second FIB fabrication as a result of the amount of the first element from the first element ion beam existing in the damaged layer being less than the threshold value.

17. A charged particle beam device comprising:

a sample stage which supports a sample;

a first element ion beam optical system unit which performs a first FIB fabrication to form a sample piece from the sample by irradiating the sample with a first element ion beam;

a second element ion beam optical system unit which performs a second FIB fabrication to remove a damaged layer formed on a surface of the sample piece by irradiating the sample piece with a second element ion beam;

an electron beam optical system unit which irradiates the sample piece with an electron beam;

an X-ray detector which detects X rays from the sample piece;

an interface receiving a threshold value for the amount of the first element from the first element ion beam existing in the damaged layer;

a fabrication terminator which terminates the second FIB fabrication; and a comparison unit comprising a processor which controls the fabrication terminator and instructs the fabrication terminator to terminate the second FIB fabrication as a result of the amount of the first element from the first element ion beam existing in the damaged layer analyzed by an output from the X-ray detector being less than the threshold value.

* * * * *